United States Patent
Takahashi et al.

(10) Patent No.: US 6,819,740 B2
(45) Date of Patent: Nov. 16, 2004

(54) X-RAY DIAGNOSIS APPARATUS HAVING A FLAT PANEL DETECTOR FOR DETECTING AN X-RAY IMAGE

(75) Inventors: Akihito Takahashi, Tochigi-ken (JP); Michitaka Honda, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 35 days.

(21) Appl. No.: 10/237,027

(22) Filed: Sep. 9, 2002

(65) Prior Publication Data

US 2003/0053592 A1 Mar. 20, 2003

(30) Foreign Application Priority Data

Sep. 11, 2001 (JP) ........................................ 2001-275700

(51) Int. Cl.[7] .............................................. H05G 1/64
(52) U.S. Cl. ........................................ 378/98.8; 378/19
(58) Field of Search .. 378/98.8, 19; 250/370.1–370.12; 348/294

(56) References Cited

U.S. PATENT DOCUMENTS 5,489,782 A * 2/1996 Wernikoff ................... 250/369
6,453,008 B1 * 9/2002 Sakaguchi et al. ......... 378/98.7

* cited by examiner

Primary Examiner—Craig E. Church
Assistant Examiner—Jurie Yun
(74) Attorney, Agent, or Firm—Oblon, Spivak, McClelland, Maier & Neustadt, P.C.

(57) ABSTRACT

An X-ray diagnosis apparatus having a flat panel detector which converts an X-ray into an electric signal, comprises extracting means for extracting a noise element, which is stable in a row direction and fluctuant in a column direction, included in an X-ray image obtained on the basis of the electric signal, and subtracting means for subtracting the noise element extracted by the extracting means from the X-ray image.

18 Claims, 7 Drawing Sheets

X-RAY DIAGNOSIS APPARATUS HAVING A FLAT PANEL DETECTOR FOR DETECTING AN X-RAY IMAGE

CROSS-REFERENCE TO RELATED APPLICATION

This application is based upon and claims the benefit of priority from prior Japanese Patent Application No. P2001-275700, filed on Sep. 11, 2001, the entire content of which is incorporated herein by reference.

FIELD OF THE INVENTION

The present invention relates to an X-ray flat panel detector which is usually used for an X-ray diagnosis apparatus and reduces a noise caused in an X-ray image generated in the detector. The present invention further relates to the X-ray diagnosis apparatus and to a method of improving the X-ray image in both of which a noise is reduced.

BACKGROUND OF THE INVENTION

An X-ray diagnosis apparatus has been used for a medical diagnosis. An X-ray diagnosis image is usually produced in a well-known manner, for example, shown as follows. X-rays enter into a patient body and a two dimensional X-ray image is produced by the difference of X-ray absorption in each tissue of a human body. The produced two-dimensional X-ray image is detected by an X-ray detector through several processes and converted to an electric signal. As a result, a visible X-ray image is obtained for a diagnosis. Recently, an X-ray flat panel detector (hereinafter referred to as FPD) has been introduced in the market as a new type of the X-ray detector.

The FPD has an array comprising a plurality of pixels in a form of a matrix. Each pixel comprises an X-ray detecting portion which converts entered X-ray signals to charge signals, a capacitor which accumulates the detected charges, and a semiconductor switch which selects to read out the detected charges from the capacitor.

When the detected charges are read out, the semiconductor switches provided in the same pixel row are switched on and off sequentially pixel row by row of the array (matrix) and the charge signals are taken out. The taken out charge signals are converted to voltage signals and amplified in amplifying portions provided in each pixel column, respectively, and are taken out as digital signals.

The digital signals usually include an offset noise (undesired offset amount) and a line artifact noise (which is a high frequency component that is stable in a row direction of the matrix and is fluctuant or fluctuates in a column direction of the matrix; the details of which are given below) as well as desirable signals converted on the basis of the entered X-ray signals. In addition, there are also a fluctuation in conversion efficiency by the X-ray detecting portions and a fluctuation in amplifying efficiency by the amplifying portions. Therefore, in order to obtain only the desirable signals based on the entered X-ray signals, it may be necessary to correct such undesired noises and fluctuations.

Practically, it is usually possible to obtain correction data for each of the offset noise, the fluctuation in conversion efficiency, and the fluctuation in amplifying efficiency in advance of an actual examination by an X-ray diagnosis apparatus. Accordingly, the obtained correction data are used for image corrections afterwards.

When, however, it comes to the line artifact noise, correction data is not typically available in advance. In general, the line artifact noise is thought to be originating from a temporal fluctuation in a signal (gate signal) for switching on/off the semiconductor switches in the same pixel row, row by row. A line (gate line) for conveying a signal for switching on/off the semiconductor switches provided in the same pixel row is provided to be insulated from a line (signal line) for transferring the charge signals accumulated in each pixel to the amplifying portion. Each signal line is commonly used for pixels in each pixel column. However, the insulation may often be practically imperfect, and this may cause an apparent stray capacitance to exist in each crossing portion of between the gate line and the signal line. Accordingly, even when it is not time to switch on the semiconductor switches provided in a pixel row, the apparent stray capacitance related to the pixel row is read out, responsive to the fluctuation of the gate signal as a noise included in the gate signal. This results in that such an apparent stray capacitance comes to be laced in the charge signals read out from the capacitor provided in each pixel. Since a noise included in the gate signal is usually different in each actual examination, the line artifact noise may usually be different in each actual examination. This is why the correction data for the line artifact noise is not typically available in advance of an actual examination by an X-ray diagnosis apparatus.

For such a line artifact noise, one solution has been presented as follows. Since the line artifact noise is temporally random and not available for preparing correction data in advance, one or more of columns of X-ray blind pixels (hereinafter referred to as dark lines) are prepared at one or both end(s) of the FPD. Information originated from a gate signal may be sampled from the dark lines during an actual examination and the sampled information is used to prepare one dimensional correction data for each pixel row. The prepared correction data is applied to a line artifact noise in real time during the actual examination.

The above method of correcting a line artifact noise may have some effect. Since, however, the above method is of a correction using one dimensional correction data for each pixel row, it still cannot solve a problem of a fluctuation of a line artifact noise in each pixel column, that is, the difference of a noise size in each pixel column even in the same pixel row.

As for causes of the fluctuation of the line artifact noise in each pixel column, there may be mentioned the following three factors: (1) accuracy of correcting the fluctuation in amplifying efficiency of the amplifying portion in each pixel column; (2) the difference of the apparent stray capacitance in each crossing portion of between the gate line and the signal line; and (3) intergradations of the line artifact noise in response with transferring distances due to a resistance or impedance component of the gate line. For example, taking the factor (3) into consideration, the larger the FPD is, the worse its correction accuracy seems to become.

Consequently, with the prior art method of correcting the line artifact noise, a preferable correction was not performed on the line artifact noise (which is temporally random) which fluctuates in each pixel column. This caused an X-ray diagnosis image to have noise remaining due to the failure of clearing the line artifact noise and noise remaining as a result of exceeding correction of the line artifact noise (collectively hereinafter referred to as remaining line artifact noise). After all, it may have resulted in a problem in an X-ray image diagnosis.

Further, the prior art correction data for the fluctuation in conversion efficiency of the X-ray detecting portions is typically obtained by calculating a fluctuation in each pixel, in advance, by using an X-ray image obtained through the pixels with X-rays evenly entered into the pixels without a subject and an image without X-rays entrance. Such correction data, however, includes a temporally unchanged artifact in a form of lines. This is because the correction data is prepared on the basis of the X-ray image including a remaining line artifact noise. Therefore if such correction data are used for correcting the fluctuation in conversion efficiency of an X-ray image, the corrected X-ray image unintentionally has a similar temporally unchanged artifact in a form of lines.

BRIEF SUMMARY OF THE INVENTION

According to a first aspect of the present invention, there is provided a flat panel detector, having a plurality of pixels in a matrix, for detecting an X-ray image, which comprises first filtering means for filtering out a high frequency in a column direction of a first X-ray image obtained through at least a portion of the pixels from the first X-ray image, first subtracting means for subtracting the image obtained by the first filtering means from the first X-ray image, second filtering means for filtering out a high frequency in a row direction of the image obtained by the first subtracting means from the image obtained by the first subtracting means, and second subtracting means for subtracting the image obtained by the second filtering means from the first X-ray image.

According to a second aspect of the present invention, there is provided a flat panel detector, having a plurality of pixels in a matrix, for detecting an X-ray image, which comprises first filtering means for filtering out, a high frequency in a column direction of a first X-ray image obtained through the pixels with an X-ray evenly entered into the pixels without a subject, from the first X-ray image, first subtracting means for subtracting the image obtained by the first filtering means from the first X-ray image, second filtering means for filtering out a high frequency in a row direction of the image obtained by the first subtracting means from the image obtained by the first subtracting means, and second subtracting means for subtracting the image obtained by the second filtering means from the first X-ray image.

According to a third aspect of the present invention, there is provided an X-ray diagnosis apparatus for converting an X-ray into an electric signal, which comprises extracting means for extracting a noise element, which is fluctuant in a column direction, included in a first X-ray image obtained on the basis of the electric signal, and subtracting means for subtracting the noise element extracted by the extracting means from the first X-ray image.

According to a fourth aspect of the present invention, there is provided a method of correcting an X-ray image detected in a flat panel detector having a plurality of pixels in a matrix, which comprises a first step of filtering out a high frequency in a column direction of the X-ray image from the X-ray image, a second step of subtracting the image obtained in the first step from the X-ray image, a third step of filtering out a high frequency in a row direction of the image obtained in the second step from the image obtained in the second step, and a fourth step of subtracting the image obtained in the third step from the X-ray image.

According to a fifth aspect of the present invention, there is provided a computer program product on which is stored a computer program for reducing a noise appearing in an X-ray image, the computer program having instructions, which when executed perform steps comprising filtering out a high frequency in a column direction of the X-ray image from the X-ray image, subtracting the image obtained by the column direction filtering step from the X-ray image, filtering out a high frequency in a row direction of the image obtained by the subtracting step from the image obtained by the subtracting, and subtracting the image obtained by the row direction filtering step from the X-ray image.

According to a sixth aspect of the present invention, there is provided a method of correcting an X-ray image obtained from an X-ray diagnosis apparatus, which comprises a step of extracting a noise element, which is stable in a row direction and fluctuant in a column direction, included in the X-ray image, and a step of subtracting the noise element extracted by the extracting step from the X-ray image.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Embodiments of the present invention will be described with reference to the accompanying drawings.

(First Embodiment)

Figure 1:
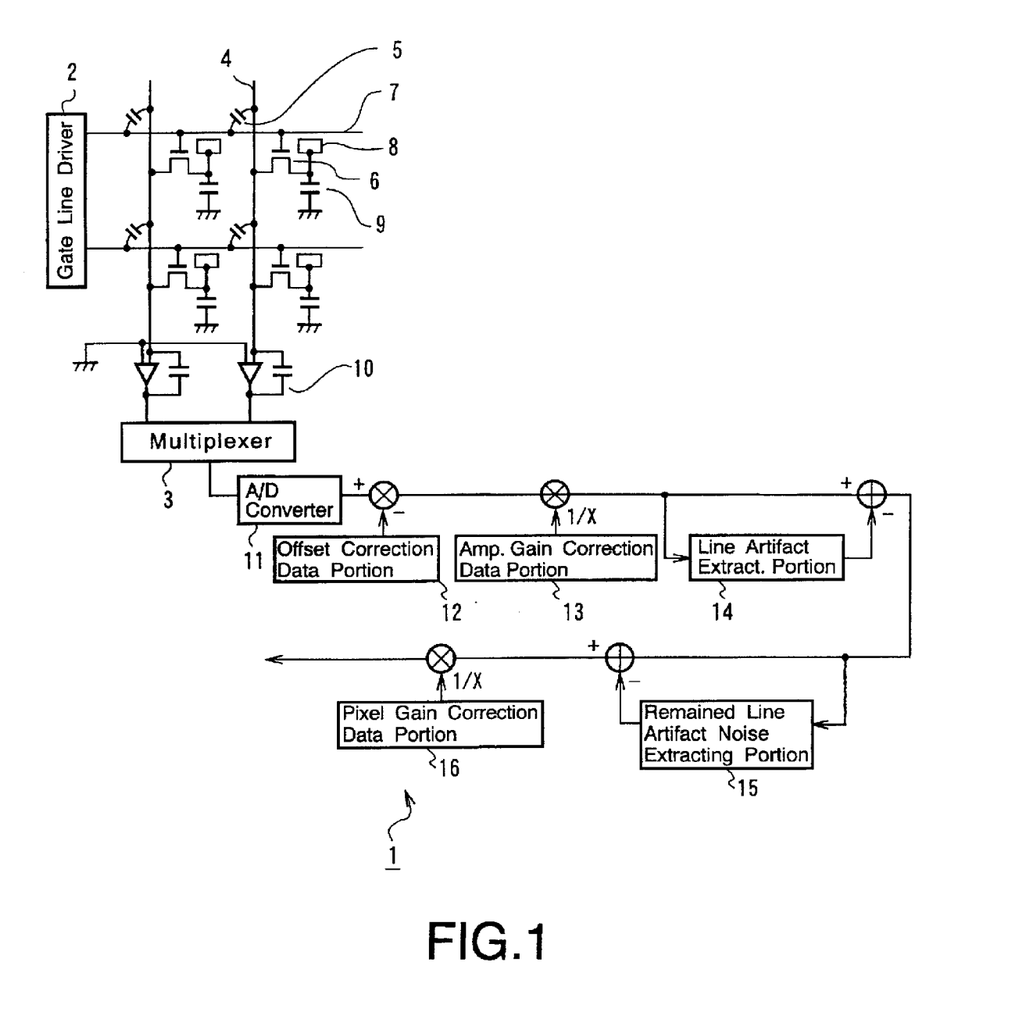
FIG. 1 is a block diagram showing an X-ray flat panel detector according to a first embodiment of the present invention.

FIG. 1 is a block diagram showing an FPD according to a first embodiment of the present invention. An X-ray diagnosis apparatus 1 may have an FPD comprising components shown in FIG. 1, for example. The FPD comprises a gate line driver 2, a multiplexer 3, signal lines 4, apparent stray capacitances 5 (each of which exists in a crossing portion of between a signal line 4 and a gate line 7), semiconductor switches 6, gate lines 7, X-ray detecting portions 8, capacitors 9, amplifying portions 10, an analog to digital converter (hereinafter referred to as A/D converter) 11, an offset correction data portion 12, an amplifier gain correction data portion 13, an line artifact noise data extracting portion 14, a remaining line artifact noise data extracting portion 15, and a pixel gain correction data portion 16.

It is obvious that the apparent stray capacitance 5 is not what is intentionally provided but exists apparently in a crossing portion of between each signal line 4 and each gate line 7 although the signal lines 4 and the gate lines 7 are provided to be mutually insulated.

The X-ray detecting portion 8 converts entered X-ray signals to charge signals. The capacitor 9 accumulates detected charges. The semiconductor switch 6 selects to read out the detected charges from the capacitor 9. One pixel comprises the X-ray detecting portion 8, the capacitor 9, and the semiconductor switch 6. A plurality of pixels are provided in a form of an array, and called an array portion.

A drain terminal of the semiconductor switch 6 in each pixel in the same column is commonly connected to the same signal line 4 and further to the amplifying portion 10 through the signal line 4. A gate terminal of the semiconductor switch 6 in each pixel in the same row is commonly connected to the same gate line 7 and further to the gate line driver 2 through the gate line 7. The gate driver 2 provides a gate signal in a form of a pulse for reading out the charge signals. The gate signal, through the gate lines 7, switches on every semiconductor switches 6 in one gate line 7 (row), and this switching is made row by row. When semiconductor switches 6 in the next gate line 7 are switched on, the semiconductor switches 6 in the current gate line 7 are switched off.

The charge signals read out by switching on the semiconductor switches 6 are converted to voltage signals and amplified in the amplifying portions 10. The amplified signals are output to the A/D converter 11 for each pixel in every column through the multiplexer 3. The output signals are converted to digital signals in the A/D converter 11, and the digital signals are to be corrected in a later stage.

The digital signals converted in the A/D converter 11 represent image data on which image corrections have not been performed yet. The image data may include some undesired components, such as an offset noise, a line artifact noise, and gain fluctuations, and so may need corrections to reduce the undesired components so as to have an image quality appropriate for a diagnosis as an X-ray diagnosis image. Each correction will be explained with reference to FIG. 2 in addition to FIG. 1.

Figure 2:
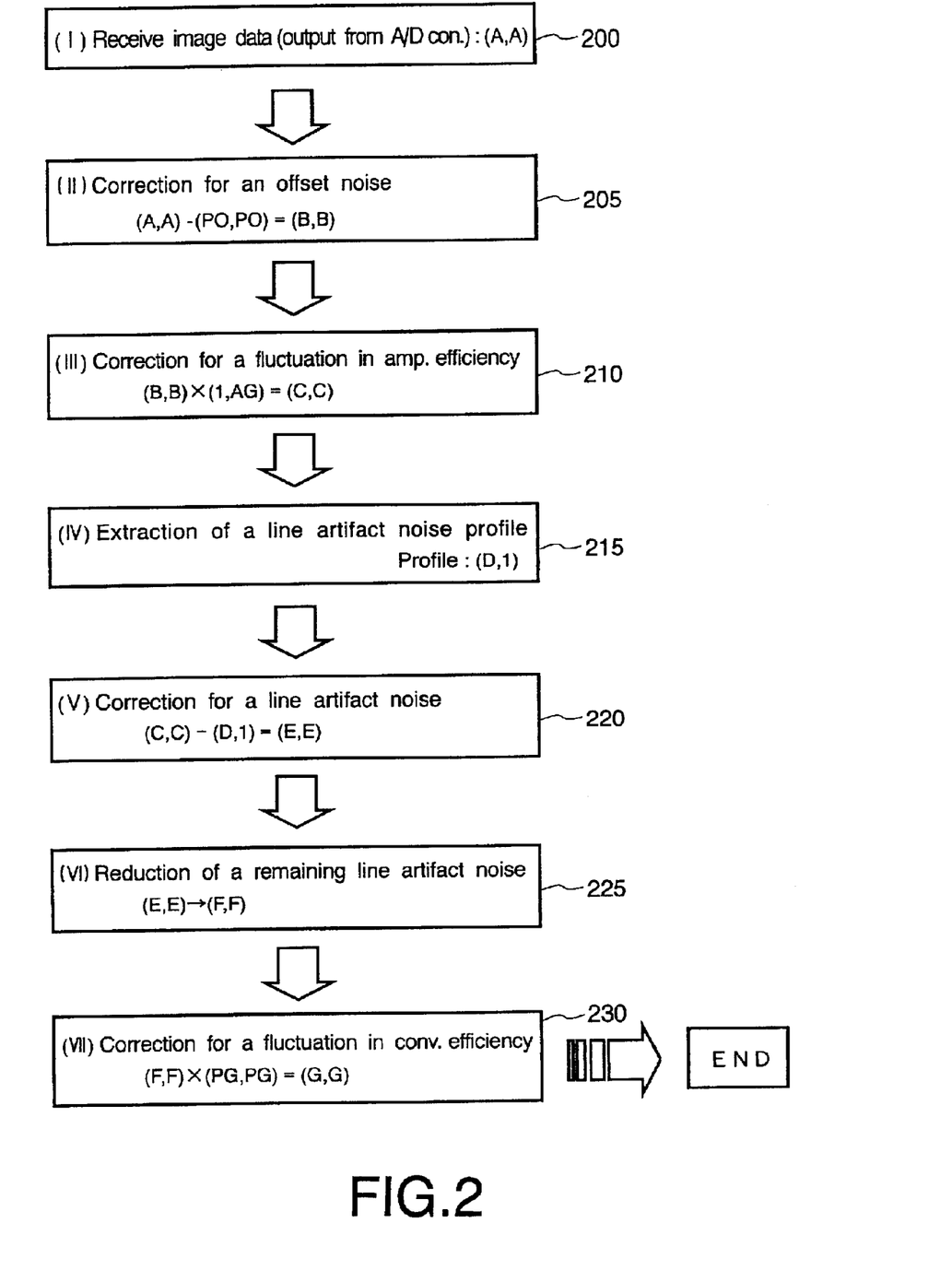
FIG. 2 is an example showing a procedure of correcting an X-ray image according to the first embodiment of the present invention.

FIG. 2 is an example showing a procedure of correcting an X-ray image according to the first embodiment of the present invention. In FIG. 2, the size of each image or data shown as, for example, (A, A), (B, B), in each process stage, is the same, except for the size of data shown as (1, AG) and (D, 1). The image is or data shown as (A, A) and (B, B) indicate images or data in different stages, respectively. The data shown as (1, AG) means data which have only one row, that is, one-dimensional data in a row direction while its column size is the same as that of others. Similarly, the data shown as (D, 1) means data which have only one column, that is, one-dimensional data in a column direction while its row size is the same as that of others.

First of all, a correction is performed on an offset noise component included in the image data. The offset noise component may basically comprise an offset noise component originated from the X-ray detecting portions 8 and the array portion, and an offset noise component originated from the amplifying portions 10.

The former may be caused by the following three charges responsive to switching of the semiconductor switches 6. The three charges are: (1) charges accumulated while X-rays are not entered; (2) leak charges from capacitors 9 in pixels which are not switched on, due to the characteristics of the semiconductor switches 6; and (3) charges accumulated in stray capacitances in lines among the semiconductor switches 6. The latter may mainly include offset noise components by circuit elements of the amplifying portions 10.

The offset noise component for each pixel may be available by temporal averaging over several frames of images without X-ray exposure in advance of an actual examination. Correction data for the offset noise component can be collected on the basis of the offset noise component. The collected correction data (hereinafter referred to as offset correction data) (PO, PO) (PO: Pixel Offset) are stored in the offset correction data portion 12.

The offset correction data (PO, PO) stored in the offset correction data portion 12 may be subtracted from image data (A, A) (Step 200) received from digital signals output of the A/D converter 11. Accordingly, an offset noise correction can be performed on the image data (A, A) and an offset corrected image (B, B) is obtained (Step 205).

The next correction may be performed for a fluctuation in amplifying efficiency by the amplifying portions 10. This fluctuation may be originated from nonuniformity of circuit elements of the amplifying portions 10. For correcting this fluctuation, it uses an amplified X-ray image obtained through the pixels with X-rays evenly entered into the pixels or an image obtained by inputting averaged charge signals to the amplifying portions 10 in a predetermined kind of form. Correction data for the fluctuation can be collected by calculating a fluctuation in each amplifying portion 10 connected to each signal line 4, in advance of an actual examination. The collected correction data for the fluctuation in amplifying efficiency (hereinafter referred to as amplifier gain correction data) (1, AG) (AG: Amplifier Gain) is one-dimensional data and is stored in the amplifier gain correction data portion 13. The offset corrected image (B, B) is multiplied by the amplifier gain correction data (1, AG). Accordingly, a correction for the fluctuation in amplifying efficiency can be performed on the offset corrected image (B, B) and an amplifier gain corrected image (C, C) is obtained (Step 210).

After obtaining the amplifier gain corrected image (C, C), another correction may be performed for a line artifact noise. This correction is the same as that explained in the background of the invention. As described before, since the line artifact noise is temporally random and not available for preparing correction data in advance, there are provided dark lines at one or both end(s) of the FPD. Information originating from a gate signal may be sampled from the dark lines during an actual examination and, with the sampled information, signals in each pixel row are averaged and so on. Accordingly, one dimensional correction data (hereinafter referred to as line artifact noise profile) (D, 1) are extracted in real time during the actual examination. This extraction is implemented in the line artifact noise data extracting portion 14 (Step 215).

The line artifact noise profile (D, 1) may be subtracted from the amplifier gain corrected image (C, C). Accordingly, a line artifact noise correction can be performed on the amplifier gain corrected image (C, C) and a line artifact noise corrected image (E, E) is obtained (Step 220).

Responsive to the line artifact noise correction, another correction related to the line artifact noise (hereinafter referred to as remaining line artifact noise reduction) may be performed. This remaining line artifact noise reduction is most related to the present invention. Here, however, only one aspect of the present invention is described as the first embodiment of the present invention.

The remaining line artifact noise reduction may be performed because, as mentioned in the background of the invention, the line artifact noise correction explained in step 220 is typically not enough to reduce minor components of the line artifact noise. In other words, it still cannot solve a problem of the difference of a noise size in each pixel column even in the same pixel row, although such line artifact noise correction has some effect for reducing major components of the line artifact noise. With the line artifact noise remained in an X-ray diagnosis image, there may be possibility of affecting a diagnosis result. The details of the remaining line artifact noise reduction will be described later with reference to FIG. 3.

For the remaining line artifact noise, remaining line artifact noise data are extracted with filtering processing in the remaining line artifact noise data extracting portion 15. The extracted remaining line artifact noise is subtracted from the line artifact noise corrected image (E, E). Accordingly, the remaining line artifact noise reduction can be performed on the line artifact noise corrected image (E, E) and a remaining line artifact noise reduced image (F, F) is obtained (Step 225).

Finally, a correction may be performed for a fluctuation in conversion efficiency by the X-ray detecting portions 8. This fluctuation may be originated from nonuniformity of thickness of layers for converting X-ray signals to charge signals and nonuniformity of membrane compositions. For correcting this fluctuation, it uses an amplified X-ray image obtained through the pixels with X-rays evenly entered into the pixels and an image without X-rays. Correction data for this fluctuation can be collected by calculating fluctuations among pixels. The collected correction data for the fluctuation in conversion efficiency (hereinafter referred to as pixel gain correction data) (PG, PG) (PG: Pixel Gain) is stored in the pixel gain correction data portion 16. The remaining line artifact noise reduced image (F, F) is multiplied by the pixel gain correction data (PG, PG). Accordingly, a correction for a fluctuation in conversion efficiency can be performed on the remaining line artifact noise reduced image (F, F) and a pixel gain corrected image (G, G) is obtained (Step 230).

With this fluctuation correction, the procedure of correcting an X-ray image by FPD is generally completed although further correction processes may be added for any deficiency, if any, in the pixel gain corrected image (G, G).

Figure 3:
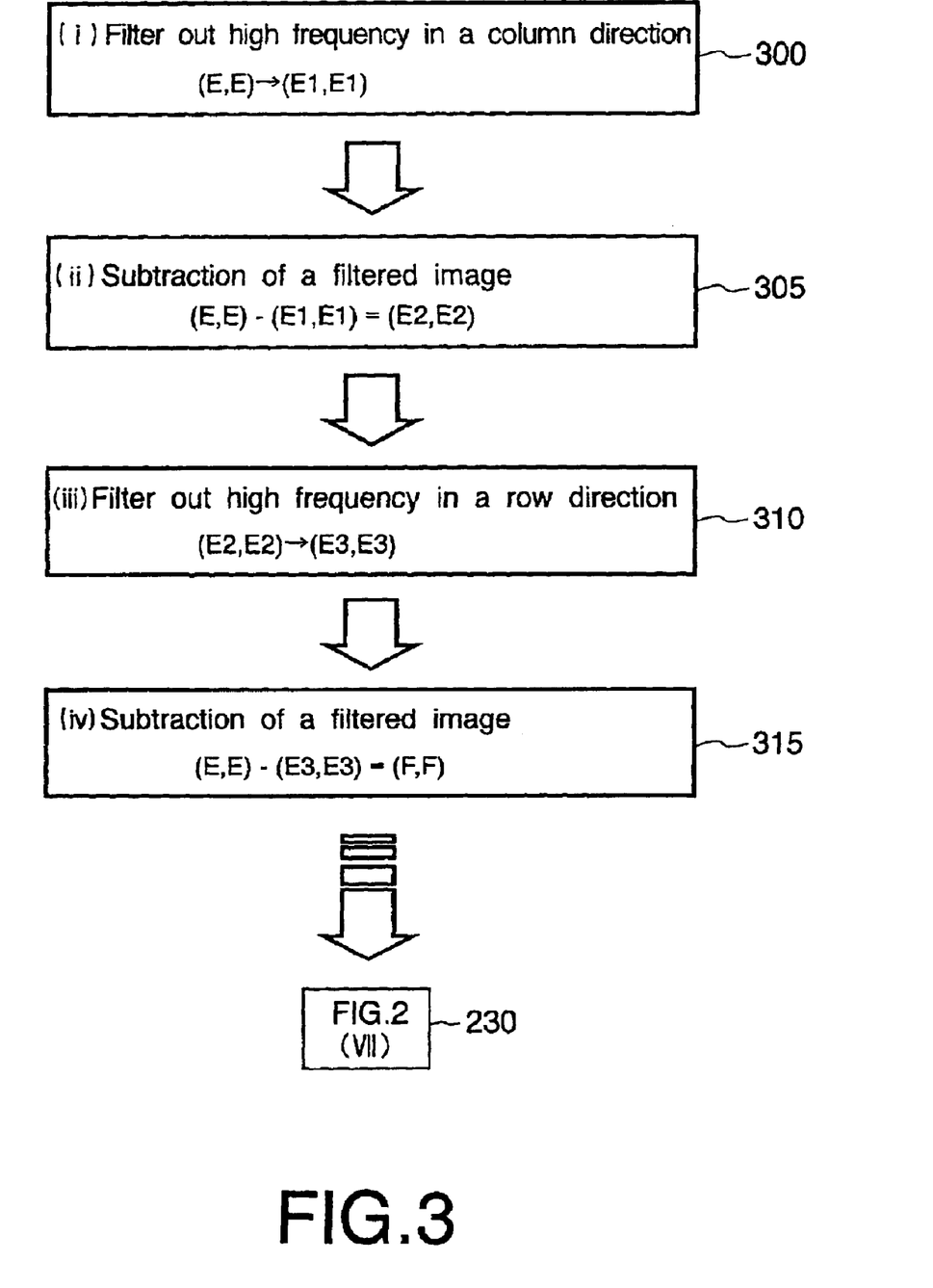
FIG. 3 is an example showing a procedure of reducing a noise caused in the X-ray image according to the first embodiment of the present invention.

With reference to FIG. 3, the remaining line artifact noise reduction will be explained below. FIG. 3 is an example showing a procedure of reducing a remaining line artifact noise caused in the X-ray image according to the first embodiment of the present invention FIG. 3 may be understood more easily by referring to FIGS. 4 to 7 which are examples showing images in each process of the procedure shown in FIG. 3 according to the first embodiment of the present invention. In FIGS. 3 to 7, images (E, E) and (F, F) represent the line artifact noise corrected image (E, E) and the remaining line artifact noise reduced image (F, F), respectively, both of which were explained in FIG. 2.

First, a filtering processing may be performed on the line artifact noise corrected image (E, E). In the filtering processing, high frequencies in a column direction of the line artifact noise corrected image (E, E) are filtered out from the line artifact noise corrected image (E, E). This is because the remaining line artifact noise is of high frequencies in a column direction while a subject for a diagnosis, such as an organ, is of quite low frequencies in a column direction. To be more precise, the remaining line artifact noise is stable in the same row (or stable in a row direction) but is (very) fluctuant at random in each row (or fluctuant in a column direction), so this noise can be of high frequencies in a column direction. On the other hand, a fluctuation of the subject is quite smoothing in each row (or smooth in a column direction), so this subject can be of quite low frequencies in a column direction.

Figure 4:
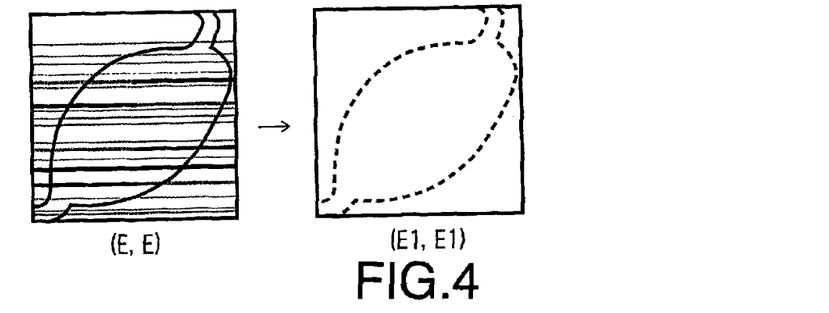
FIG. 4 is an example showing images in a first process of the procedure shown in FIG. 3 according to the first embodiment of the present invention.

Therefore, by filtering out high frequencies in a column direction of the line artifact noise corrected image (E, E), the remaining line artifact noise which remains in the line artifact noise corrected image (E, E) may be reduced at high rates and the remaining line artifact noise temporary-reduced image (E1, E1) is obtained in step 300 (FIG. 4).

In this filtering processing for removing predetermined high frequencies, it may be a basic technique to use the Fourier transformation. For example, the line artifact noise corrected image (E, E) is transformed to an image represented by frequency components by the Fourier transformation. The filtering by a predetermined filtering characteristics (here, removal of high frequencies in a column direction) is performed on the Fourier transformed image. The filtered image is retransformed by the Fourier inverse transformation and the image (E1, E1) is obtained.

Such processing, however, is complicated and requires a lot of time. Instead of using the above technique, it may be easier and quicker to prepare a filter obtained by transforming the filtering characteristics by the Fourier inverse transformation in advance (hereinafter referred to as operator), and to perform a convolution operation on the line artifact noise corrected image (E, E) and obtain the image (E1, E1). The operator may be coefficients to perform a processing which substantially implements a filtering processing.

Figure 8:
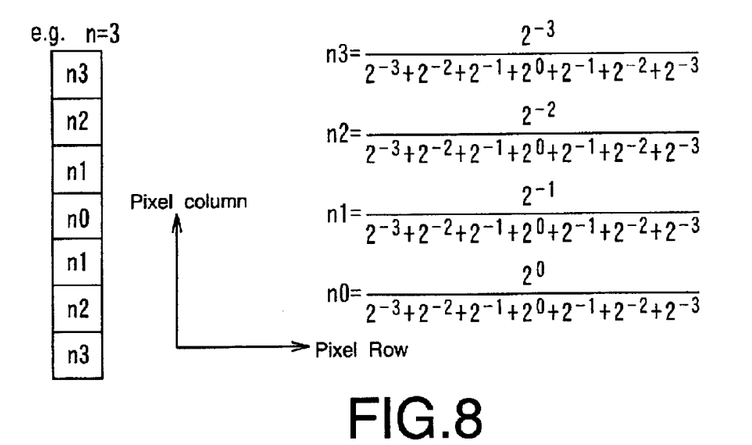
FIG. 8 is an example showing a filter which may be used in the first process of the procedure shown in FIG. 3 according to the first embodiment of the present invention.

When such an operator is used for the above processing, those skilled in the digital filtering art will appreciate that the filter size of the operator may be (2n+1, 1) (n: 0 or more than 0). FIG. 8 is an example showing a filter which may be used in step 300 according to the first embodiment of the present invention. Here, n=3 is taken as an example. In the case of n=3, the filter size (2n+1, 1) is (7, 1). In FIG. 8, n0 indicates a pixel targeted for the processing. Since the filtering processing can be performed over the whole image (the line artifact noise corrected image (E, E)), the targeted pixel is changed one to another. N1s indicate pixels next to the n0. Similarly, n2s indicate pixels next but one to the n0. This is an example using weighted filtering. The targeted pixel n0 is most weighted, and the farther the pixel is from the targeted pixel n0, the less the pixel is weighted. This is because, since this filtering determines a targeted pixel by averaging the targeted pixel with its neighboring 6 pixels, the targeted pixel should be the most important and the targeted pixel may contain a component of the subject for diagnosis as well as the remaining line artifact noise. The factors for each weighting and the operator's size are not limited to examples shown in FIG. 8, but may be determined appropriately for each case. Although it is preferable that the greater the value of n is, the more correctly the filtering processing will be performed, in practice, the value of n may be determined in consideration of characteristics of a line artifact noise and a processing speed, and so on.

The image (E1, E1) obtained in a process of step 300 is an image with a remaining line artifact noise reduced. The image (E1, E1) is, however, also reduced a part of information of a subject image to be diagnosed, such as an organ, by the filtering in the process of step 300. Therefore, the image (E1, E1) may still be good enough to be used as the remaining line artifact noise reduced image (F, F). This usually means a necessity of further processing, such as those shown in the following processes of step 305 to step 315.

Figure 5:
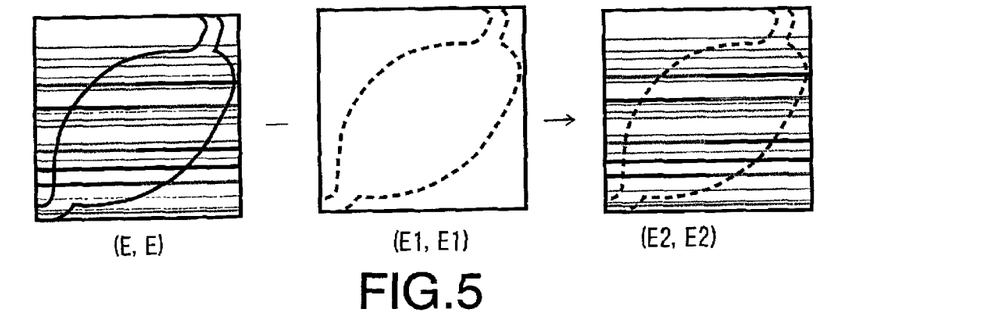
FIG. 5 is an example showing images in a second process of the procedure shown in FIG. 3 according to the first embodiment of the present invention.

The obtained image (E1, E1) may be subtracted from the line artifact noise corrected image (E, E) and accordingly an image (E2, E2) is obtained in step 305 (FIG. 5). This image (E2, E2) may include the part of information of the subject image to be diagnosed, which was reduced from the image (E1, E1) in the process of step 300, as well as the remaining line artifact noise included in the line artifact noise corrected image (E, E). The part of information of the subject image included in the image (E2, E2) may be an X-ray signal image only in a pixel row direction and comprise information of an outline of the subject image to be diagnosed.

Next, high frequencies in a row direction of the image (E2, E2) may be filtered out from the image (E2, E2). This is performed for the purpose of reducing (or removing) the part of information of the subject image included in the image (E2, E2), by utilizing characteristics of a line artifact noise which has the approximately same component in each pixel row.

Figure 6:
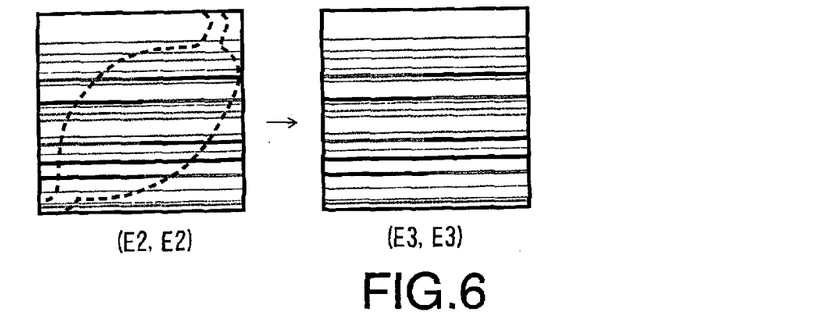
FIG. 6 is an example showing images in a third process of the procedure shown in FIG. 3 according to the first embodiment of the present invention.

By the filtering described above, an image in which the subject image included in the image (E2, E2) may be reduced (or removed) from the image (E2, E2) is obtained as an image having substantially only the remaining line artifact noise (E3, E3) (Step 310) (FIG. 6). In other words, the remaining line artifact noise has been extracted.

For the filtering explained above, the Fourier transformation can be performed. Here, however, as similar to the process of step 300, another operator may be used for the filtering. The image (E3, E3) may be obtained by performing a convolution operation on the image (E2, E2) with the operator. The filter size of the operator in the process of step 310 may be (1, 2m+1) (m: 0 or more than 0).

Figure 9:
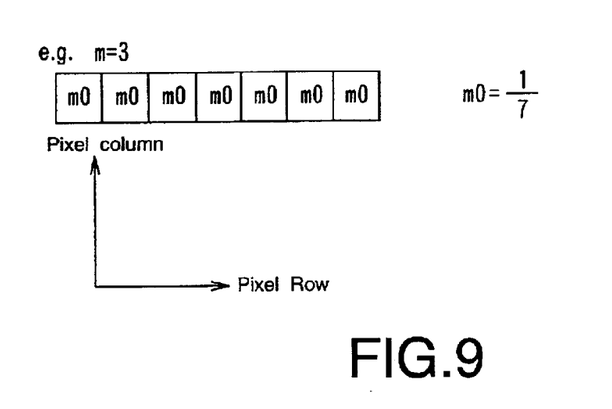
FIG. 9 is an example showing a filter which may be used in the third process of the procedure shown in FIG. 3 according to the first embodiment of the present invention.

FIG. 9 is an example showing a filter which may be used in step 310 according to the first embodiment of the present invention. Here, m=3 is taken as an example. In the case of m=3, the filter size (1, 2m+1) is (1, 7). In this filtering processing, an averaged weighting may be made for a targeted pixel and its adjacent pixels. In FIG. 9, the targeted pixel and its adjacent 6 pixels are all represented, for example, as m0. The m0 is given a factor, ⅐ (an seventh). Therefore, the above described filtering is a simply averaged filtering in a pixel row direction. The reason is as follows. Since the subject image to be diagnosed in the image (E2, E2) may comprise information of an outline of the subject image, the outline may be smoothed by simple averaging and accordingly be removed from the image (E2, E2). On the other hand, the remaining line artifact noise has characteristics of having the approximately same component in each pixel row, and so the remaining line artifact noise may remain even by the simply averaged filtering in the pixel row direction.

Usually an actual clinical image does not include an X-ray signal image over hundreds of columns in a row, and so such an X-ray signal image can be distinguished from the remaining line artifact noise component. Therefore, a value of 'm' for determining the filter size may be determined in accordance with characteristics of an X-ray signal image in an actual clinical image.

Further, in the averaged filtering processing, if there is even one pixel which has an extraordinary value due to the pixel deficiency, the averaged result cannot represent a correct value. To avoid such a result, it may be preferable to set a threshold level and to select pixels, with over the threshold level, to be averaged.

Figure 7:
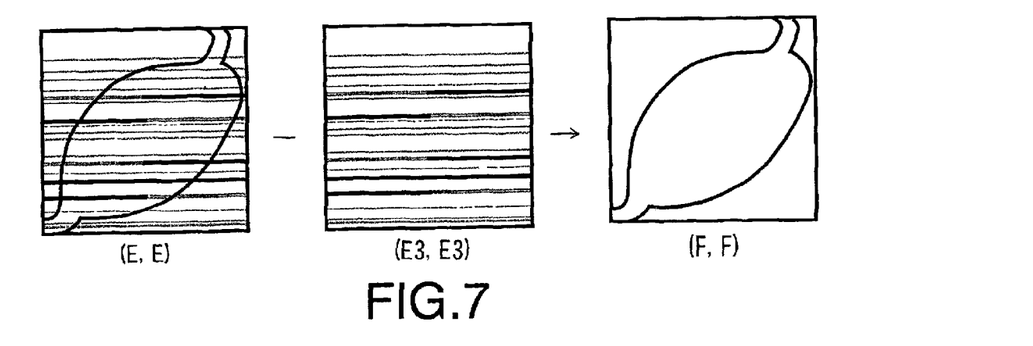
FIG. 7 is an example showing images in a fourth process of the procedure shown in FIG. 3 according to the first embodiment of the present invention.

Finally, the image (E3, E3) obtained in the process of step 310 may be subtracted from the line artifact noise corrected image (E, E) since the image (E3, E3) has substantially or almost only the remaining line artifact noise. Accordingly, an image from which the remaining line artifact noise has been reduced (or removed), that is, the remaining line artifact noise reduced image (F, F), is obtained in step 315 (FIG. 7).

The obtained remaining line artifact noise reduced image (F, F) may be multiplied by the pixel gain correction data (PG, PG) in the process of step 230. Accordingly, a quality improved X-ray diagnosis image (the pixel gain corrected image (G, G)) is obtained.

(Second Embodiment)

In the first embodiment of the present invention, the pixel gain correction data (PG, PG) to be multiplied by the remaining line artifact noise reduced image (F, F) was explained as data obtained in a conventional manner. Since, however, pixel gain correction data are prepared with a use of an X-ray image, even if a remained line noise artifact noise reduced image was obtained, there would be still a possibility of that a pixel gain corrected image may result in including a remaining line artifact noise. Although the pixel gain corrected image (G, G), according to the first embodiment of the present invention, has a better quality than equivalents in a prior art, the pixel gain corrected image (G, G) cannot sufficiently take advantage of the effect of the remaining line artifact noise reduction explained in the first embodiment of the present invention.

For example, there would be a possibility of causing a temporally unchanged artifact in a form of lines in the pixel gain corrected image (G, G) if an image used fur preparing the pixel gain correction data (PG, PG) included a remaining line artifact noise.

According to a second embodiment of the present invention, the remaining line artifact noise reduction is applied to the preparation of pixel gain correction data. This makes it possible to present an X-ray diagnosis image with a better quality. The second embodiment of the present invention will be described with reference to FIGS. 10 and 11.

Figure 10:
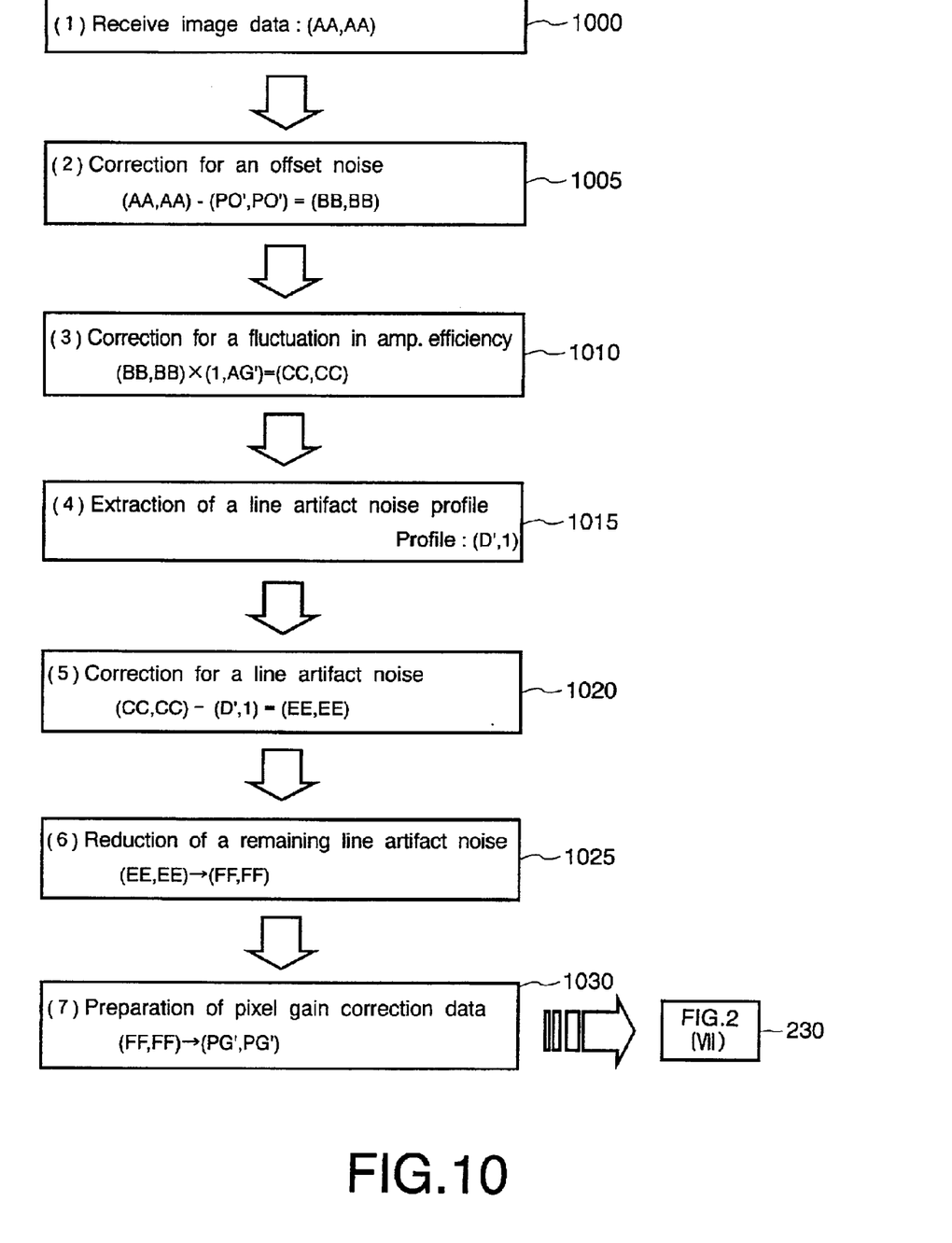
FIG. 10 is an example showing a procedure of correcting an X-ray image according to a second embodiment of the present invention.

FIG. 10 is an example showing a procedure of correcting an X-ray image according to a second embodiment of the present invention. An X-ray image for pixel gain correction data may be prepared with several corrections including a remaining line artifact noise reduction so as to have an improved image quality. FIG. 10 is basically similar to FIG. 2. Steps 1000–1025 correspond to step 200–225.

One of the differences from the first embodiment of the present invention is image data to be used in step 1000. Image data (AA, AA) to be used for pixel gain correction data are obtained through pixels of the FPD with X-rays evenly entered into the pixels without a subject. Offset correction data (PO', PO') may be subtracted from the image data (AA, AA). Accordingly, an offset noise correction can be performed on the image data (AA, AA) and an offset corrected image (BB, BB) is obtained in step 1005. It may be preferable to obtain the image data (AA, AA) by temporal averaging over several frames of images, for example, in order to reduce a temporally random noise including a line artifact noise included in the image data (AA, AA).

Next, the offset corrected image (BB, BB) may be multiplied by amplifier gain correction data (1, AG'). Accordingly, a correction for a fluctuation in amplifying efficiency can be performed on the offset corrected image (BB, BB) and an amplifier gain corrected image (CC, CC) is obtained in step 1010.

After the correction for a fluctuation in amplifying efficiency, a line artifact noise profile (D', 1) (Step 1015) may be subtracted from the amplifier gain corrected image (CC, CC). Accordingly, a line artifact noise correction can be performed on the amplifier gain corrected image (CC, CC) and a line artifact noise corrected image (EE, EE) is obtained in step 1020.

Extracted remaining line artifact noise data may be subtracted from the line artifact noise corrected image (EE, EE) (Details will be explained later). Accordingly, a remaining line artifact noise reduction can be performed on the line artifact noise corrected image (EE, EE) and a remaining line artifact noise reduced image (FF, FF) is obtained in step 1025.

Finally, pixel gain correction data (PG', PG') are obtained on the basis of the remaining line artifact noise reduced image (FF, FF) and an image without an X-rays entrance or exposure in step 1030.

The remaining line artifact noise reduced image (FF, FF) can basically be prepared in a procedure similar to that shown in FIG. 3. In the reduction of the remaining line artifact noise included in pixel gain correction data, a weighted filter (operator) may be possibly used as similar to the first embodiment of the present invention. Since, however, the image data (AA, AA) to be used for the pixel gain correction data (PG', PG') is obtained through pixels of the FPD with X-rays evenly entered into the pixels without a subject, a simply averaged filter may be applied to the filtering processing in step 300.

Figure 11:
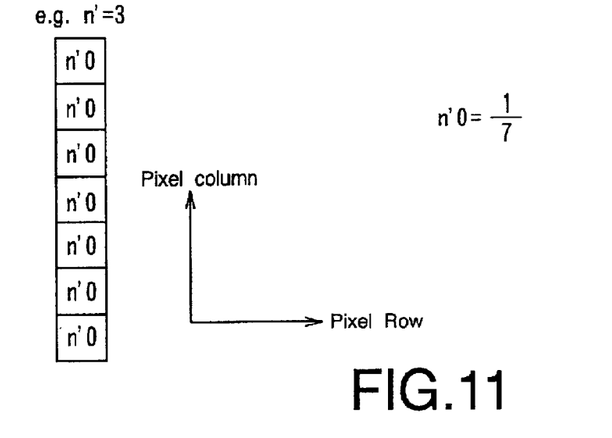
FIG. 11 is an example showing a filter which may be used in the first process of the procedure shown in FIG. 3 according to the second embodiment of the present invention.

FIG. 11 is an example showing an operator which may be used in the process of step 300 according to the second embodiment of the present invention. The size of the operator may be (2n'+1, 1) (n': 0 or more than 0). Here, n'=3 is taken as an example. In the case of n'=3, the size (2n'+1, 1) is (7, 1). In this filtering processing, an averaged weighting may be made for a targeted pixel and its adjacent pixels. In FIG. 11, the targeted pixel and its adjacent 6 pixels are all represented, for example, as n'0. The n'0 is given a factor, $\frac{1}{7}$ (a seventh). Therefore, the above described filtering is a simply averaged filtering in a pixel column direction. The reason is as follows.

Since the image data (AA, AA) which is a base of the pixel gain correction data (PG', PG') is obtained through pixels of the FPD with X-rays evenly entered into the pixels without a subject. In addition, judging that the cause of the fluctuation in conversion efficiency by the X-ray detecting portions 8 may be that described in the explanation of step 230, the fluctuation can be modest over a wide range. Accordingly, it may be appropriate and more effective to use such a simply averaged filter so as to reduce the remaining line artifact noise to be included in the pixel gain correction data (PG', PG'). The greater the n' is, the more effectively the reduction may be performed, if the processing time is allowed, since a subject image (or an X-ray signal image) is not included in the image data (AA, AA).

As explained above, according to the second embodiment of the present invention, the pixel gain correction data (PG', PG') may be prepared on the basis of the remaining line artifact noise reduced image (FF, FF), through the offset noise correction (Step 1005), the correction for a fluctuation in amplifying efficiency (Step 1010), the line artifact noise correction (Steps 1015 and 1020), and the remaining line artifact noise reduction (Step 1025). Consequently, a temporally unchanged artifact in a form of lines, which appeared in the X-ray diagnosis image in a prior art, can be reduced in a pixel gain corrected image (i.e. an X-ray diagnosis image) obtained through the correction with the pixel gain correction data described above.

Further, if the pixel gain correction data (PG', PG') according to the second embodiment of the present invention is used as the pixel gain correction data (PG, PG) according to the first embodiment of the present invention, it may be possible to obtain an X-ray diagnosis image in a further better quality with reduction of a remaining line artifact noise which is temporally random and a temporally unchanged artifact in a form of lines. Therefore, it may lead to improvement of the efficiency and accuracy in X-ray diagnosis images interpretation and to prevention of the misdiagnosis.

(Third Embodiment)

In the first embodiment of the present invention, the remaining line artifact noise reduction has been performed on an image obtained through the offset noise correction, the correction for a fluctuation in amplifying efficiency, and the line artifact noise correction. Regarding an image for the remaining line artifact noise reduction, an embodiment of the present invention may not be limited to such an embodiment.

Figure 12:
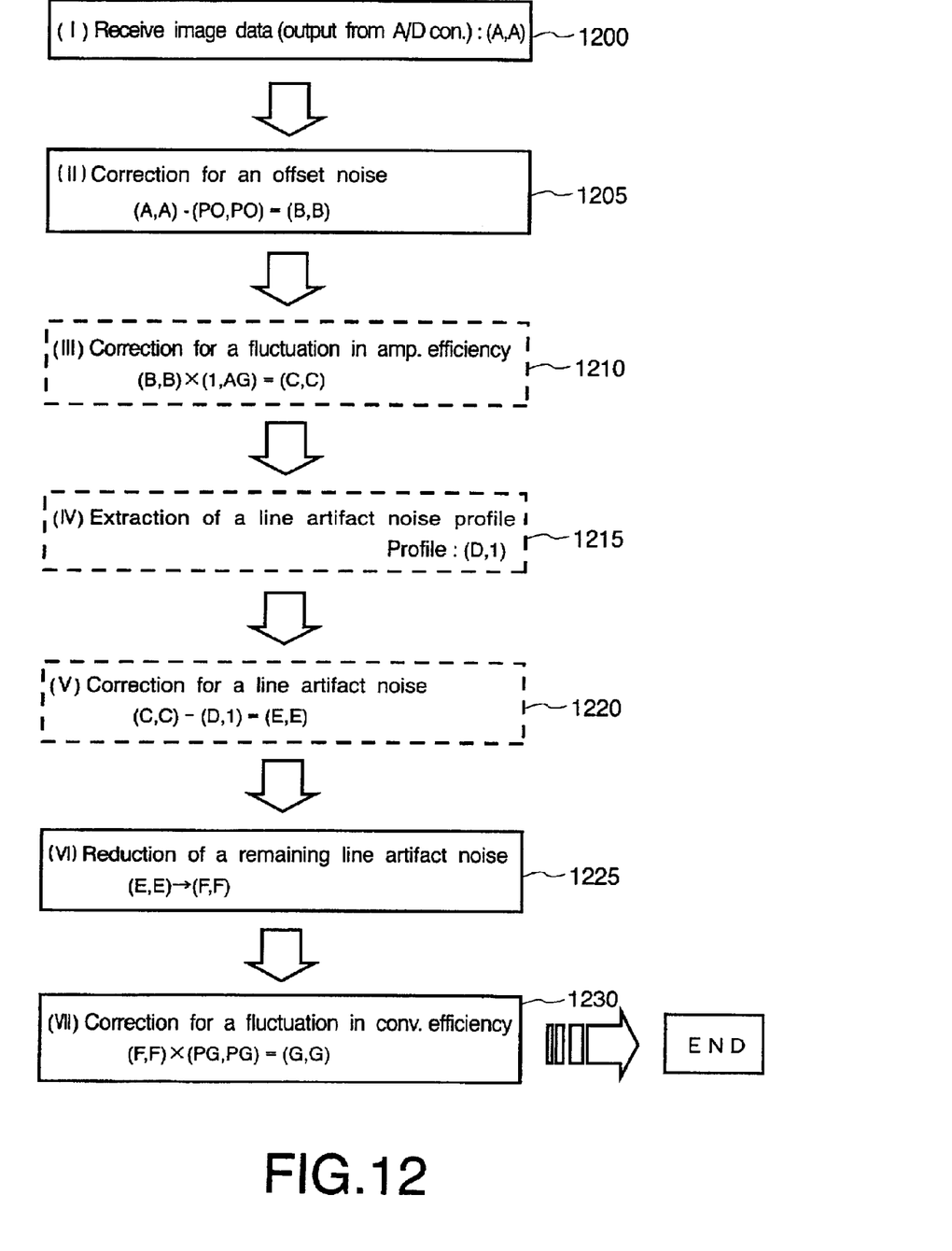
FIG. 12 is an example showing a procedure of correcting an X-ray image according to a third embodiment of the present invention.

FIG. 12 is an example showing a procedure of correcting an X-ray image according to a third embodiment of the present invention. Depending on the amount of a noise included in an image for the remaining line artifact noise reduction, one or more of the correction processing represented with the dotted lines in FIG. 12 can be omitted. The correction processing represented with the dotted lines are the correction for a fluctuation in amplifying efficiency shown in step 1210, and the line artifact noise correction shown in steps 1215 and 1220.

To be more precise, if it is judged that the fluctuation in amplifying efficiency and the line artifact noise are not so outstanding that the correction for those may not be required, such a correction may not be needed in practice. In this case, the remaining line artifact noise reduction can be performed on the offset corrected image (B, B) without the correction for a fluctuation in amplifying efficiency and the line artifact noise correction. In the remaining line artifact noise reduction, (E, E) in step 1225 and FIG. 3 may be read as (B, B).

Similarly, if it is judged that the line artifact noise is not so outstanding that the correction for that may not be required, such a correction may not be needed in practice. In this case, the remaining line artifact noise reduction can be performed on the amplifier gain corrected image (C, C) without the line artifact noise correction. In the remaining line artifact noise reduction, (E, E) in step 1225 and FIG. 3 may be read as (C, C).

Regarding the line artifact noise correction, if the correction was performed on an image which does not include an outstanding line artifact noise, there would be a possibility that a greater line artifact noise may appear in a line artifact noise corrected image as a result of the line artifact noise correction. Therefore, in such a case, it would be better to perform only a remaining line artifact noise reduction without the line artifact noise correction.

According to the embodiments of the present invention described above, it may be possible to reduce a remaining line artifact noise which is temporally random and was not reduced (or removed) and remained in an X-ray diagnosis image in a prior art.

Further, it may also be possible to reduce a remaining line artifact noise in pixel gain correction data. This may result in reducing a temporally unchanged artifact in a form of lines in an X-ray diagnosis image, which is influenced by the remaining line artifact noise in the pixel gain correction data.

Still further, in the embodiments of the present invention, the FPD or the X-ray diagnosis apparatus may have a random access memory (RAM), which can receive and store computer programs and applications as computer readable instructions in a temporary and/or non-volatile state. The FPD or the X-ray diagnosis apparatus may further have a hard disk drive for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions which when executed may implement any embodiment of the present invention.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention.

What is claimed is:

1. A flat panel detector, having a plurality of pixels in a matrix, for detecting an X-ray image, the detector comprising:
   first filtering means for filtering out a high frequency in a column direction of a first X-ray image obtained through at least a portion of the pixels from the first X-ray image, the high frequency being stable in a row direction and fluctuant in the column direction;
   first subtracting means for subtracting the image obtained by the first filtering means from the first X-ray image;
   second filtering means for filtering out a high frequency in a row direction of the image obtained by the first subtracting means from the image obtained by the first subtracting means; and
   second subtracting means for subtracting the image obtained by the second filtering means from the first X-ray image.

2. The detector according to claim 1, wherein the first filtering means is a weighted filter.

3. The detector according to claim 1, wherein the second filtering means is an averaged filter.

4. The detector according to claim 1, further comprising offset correction means for correcting an offset noise of an initial image obtained through the pixels, and wherein the first X-ray image is obtained by the offset correction means.

5. The detector according to claim 1, further comprising gain correction means for correcting a gain of an initial image obtained through the pixels, and wherein the first X-ray image is obtained by the gain correction means.

6. The detector according to claim 1, further comprising noise correction means for correcting a row noise included in an initial image obtained through the pixels, the row noise appearing in the row direction of the initial image according to noise information resulting from a signal applied to each pixel to read out a blacked-out column of the detector in each row, and wherein the first X-ray image is obtained by the noise correction means.

7. The detector according to claim 1, wherein the first filtering means does not filter out any frequency in the row direction of the first X-ray image from the first X-ray image.

8. The detector according to claim 1, further comprising:
   third filtering means for filtering out, a high frequency in the column direction of a second X-ray image obtained through the pixels with an X-ray evenly entered into the pixels without a subject, from the second X-ray image;
   third subtracting means for subtracting the image obtained by the third filtering means from the second X-ray image;
   fourth filtering means for filtering out a high frequency in the row direction of the image obtained by the third subtracting means from the image obtained by the third subtracting means;
   fourth subtracting means for subtracting the image obtained by the fourth filtering means from the second X-ray image; and
   multiplying means for multiplying the image obtained by the second subtracting means by pixel gain correction data obtained on the basis of the image obtained by the fourth subtracting means and an image without an X-ray exposure.

9. The detector according to claim 8, wherein the third filtering means and the fourth filtering means are averaged filters.

10. A flat panel detector, having a plurality of pixels in a matrix, for detecting an X-ray image, the detector comprising:
    first filtering means for filtering out, a high frequency in a column direction of a first X-ray image obtained through the pixels with an X-ray evenly entered into the pixels without a subject, from the first X-ray image, the high frequency being stable in a row direction and fluctuant in the column direction;
    first subtracting means for subtracting the image obtained by the first filtering means from the first X-ray image;
    second filtering means for filtering out a high frequency in a row direction of the image obtained by the first subtracting means from the image obtained by the first subtracting means; and
    second subtracting means for subtracting the image obtained by the second filtering means from the first X-ray image.

11. The detector according to claim 10, wherein the first filtering means and the second filtering means are averaged filters.

12. An X-ray diagnosis apparatus for converting an X-ray into an electric signal, the apparatus comprising:
    a detector, having a plurality of pixels in a matrix, for detecting an X-ray image;
    extracting means for extracting a noise element, which is stable in a row direction and fluctuant in a column direction, included in a first X-ray image obtained on the basis of the electric signal; and
    subtracting means for subtracting the noise element extracted by the extracting means from the first X-ray image.

13. The apparatus according to claim 12, wherein the extracting means is further operative to perform:
    a first step of filtering out a high frequency in a column direction of the first X-ray image from the first X-ray image;

a second step of subtracting the image obtained in the first step from the first X-ray image; and a third step of filtering out a high frequency in a row direction of the image obtained in the second step from the image obtained in the second step, and wherein the subtracting means performs a step of subtracting the image obtained in the third step from the first X-ray image.

14. A method of correcting an X-ray image detected in a flat panel detector having a plurality of pixels in a matrix, the method comprising:

a first step of filtering out a high frequency in a column direction of the X-ray image from the X-ray image, the high frequency being stable in a row direction and fluctuant in the column direction;

a second step of subtracting the image obtained in the first step from the X-ray image;

a third step of filtering out a high frequency in a row direction of the image obtained in the second step from the image obtained in the second step; and a fourth step of subtracting the image obtained in the third step from the X-ray image.

15. A computer-readable medium on which is stored a computer program for reducing a noise appearing in an X-ray image obtained from an X-ray apparatus including a detector having a plurality of pixels in a matrix, the computer program having instructions, which when executed perform steps comprising:

filtering out a high frequency in a column direction of the X-ray image from the X-ray image, the high frequency being stable in a row direction and fluctuant in the column direction;

subtracting the image obtained by the column direction filtering step from the X-ray image;

filtering out a high frequency in a row direction of the image obtained by the subtracting from the image obtained by the subtracting step; and subtracting the image obtained by the row direction filtering step from the X-ray image.

16. A method of correcting an X-ray image obtained from an X-ray diagnosis apparatus including a detector having a plurality of pixels in a matrix, the method comprising:

a step of extracting a noise element, which is stable in a row direction and fluctuant in a column direction, included in the X-ray image; and a step of subtracting the noise element extracted by the extracting step from the X-ray image.

17. A computer-readable medium on which is stored a computer program for reducing a noise appearing in an X-ray image obtained from an X-ray apparatus including a detector having a plurality of pixels in a matrix, the computer program having instructions, which when executed perform steps comprising:

extracting a noise element, which is stable in a row direction and fluctuant in a column direction, included in the X-ray image; and subtracting the noise element extracted by the extracting step from the X-ray image.

18. An X-ray diagnosis apparatus, comprising:

a generator configured to generate an X-ray;

a flat panel detecting component, including a plurality of pixels in a matrix, configured to detect an X-ray signal resulting from the X-ray generation through a least a portion of the pixels; and a processing component configured to process the X-ray signal so as to obtain an X-ray image, the processor including:

first filtering means for filtering out a high frequency in a column direction of a first X-ray image obtained based on the X-ray signals from the first X-ray image, the high frequency being stable in a row direction and fluctuant in the column direction:

first subtracting means for subtracting the image obtained by the first filtering means from the first X-ray image;

second filtering means for filtering out a high frequency in a row direction of the image obtained by the first subtracting means from the image obtained by the first subtracting means; and second subtracting means for subtracting the image obtained by the second filtering means from the first X-ray image so as to obtain the X-ray image.

* * * * *